(12) United States Patent
Dreisoerner

(10) Patent No.: US 8,555,707 B2
(45) Date of Patent: Oct. 15, 2013

(54) DEVICE FOR RAPID TESTING OF THE QUALITY OF CEREALS, GRITS AND FLOURS BY MEASURING THE AGGREGATION OF GLUTEN

(75) Inventor: Jens Dreisoerner, Luebbecke (DE)

(73) Assignee: Brabender GmbH & Co. KG, Duisburg (DE)

( * ) Notice: Subject to any disclaimer, the term of this patent is extended or adjusted under 35 U.S.C. 154(b) by 0 days.

(21) Appl. No.: 13/066,262

(22) Filed: Apr. 11, 2011

(65) Prior Publication Data

US 2011/0247402 A1 Oct. 13, 2011

Related U.S. Application Data

(62) Division of application No. 12/083,174, filed as application No. PCT/DE2006/001718 on Sep. 28, 2006, now Pat. No. 7,958,773.

(30) Foreign Application Priority Data

Oct. 7, 2005 (DE) .......................... 10 2005 048 184

(51) Int. Cl.
*G01N 11/14* (2006.01)
(52) U.S. Cl.
USPC ............................ 73/54.31; 73/54.28; 73/866
(58) Field of Classification Search
USPC ................... 73/54.28, 54.31, 866; 366/349
See application file for complete search history.

(56) References Cited

U.S. PATENT DOCUMENTS

| | | | |
|---|---|---|---|
| 2,572,375 A * | 10/1951 | Traugott | 366/315 |
| 2,805,843 A * | 9/1957 | Block | 366/343 |
| 3,503,344 A * | 3/1970 | Sternberg | 366/99 |
| 4,293,854 A | 10/1981 | Gookins et al. | |
| 5,102,229 A * | 4/1992 | Wada et al. | 366/294 |
| 5,513,912 A * | 5/1996 | Lotz et al. | 366/349 |
| 5,664,883 A * | 9/1997 | Tomassini | 366/325.93 |
| 6,557,397 B2 | 5/2003 | Langsch | |
| 6,652,137 B1 * | 11/2003 | Bosch et al. | 366/288 |

FOREIGN PATENT DOCUMENTS

| | | |
|---|---|---|
| DE | 233 423 | 2/1986 |
| DE | 198 28 667 | 1/1999 |
| GB | 1 217 329 | 12/1970 |
| GB | 2 326 723 | 12/1998 |
| GB | 2326723 A * | 12/1998 |

(Continued)

OTHER PUBLICATIONS

International Search Report of PCT/DE2006/001718.
Botterbrodt et al., "Qualitätsbeschreibung von Mehlen für nicht hefegelockerte Feine Backwaren (Flachwaffeln, Hartkekse, Mürbkekse)*)," ["Quality description of flours for fine baked goods not loosened with yeast"] in Getreide Mehl und Brot [Grain, Flour, and Bread], Issue 52, 1998, pp. 103-109.

(Continued)

*Primary Examiner* — Hezron E Williams
*Assistant Examiner* — Nashmiya Fayyaz
(74) *Attorney, Agent, or Firm* — Collard & Roe, P.C.

(57) ABSTRACT

A method and a device for rapid testing of the quality of cereals, grits and flours measures the aggregation of gluten. The sample to be tested in aqueous solution/suspension containing mineral salts and/or acids and/or liquors in a specific amount in a sample cup is stirred with an electrically driven stirring paddle and the resistance opposed to the paddle by the sample during the stirring process is measured, the torque loads acting on the rotatably mounted electric drive motor being measured from the beginning of the stirring process using extensometric gauges, the measurement being completed once the maximum rotating torque is reached and the measuring process being monitored, controlled and analyzed by software.

3 Claims, 5 Drawing Sheets

(56) References Cited

FOREIGN PATENT DOCUMENTS

| | | |
|---|---|---|
| JP | 05-056744 | 3/1993 |
| JP | 05-212678 | 8/1993 |
| SU | 1 392 453 | 4/1988 |

OTHER PUBLICATIONS

Hanneforth et al., "Mehle fur besondere Verwendungszwecke," Getreide Mehl und Brot [Grain, Flour, and Bread], Issue 51, 1997, pp. 227-231.

* cited by examiner

DEVICE FOR RAPID TESTING OF THE QUALITY OF CEREALS, GRITS AND FLOURS BY MEASURING THE AGGREGATION OF GLUTEN

CROSS REFERENCE TO RELATED APPLICATIONS

This application is a divisional of and Applicant claims priority under 35 U.S.C. §§120 and 121 on U.S. application Ser. No. 12/083,174 filed on Apr. 7, 2008, which application is a national stage application under 35 U.S.C. §371 of PCT Application No. PCT/DE2006/001718 filed Sep. 28, 2006, which claims priority under 35 U.S.C. §119 on German Patent Application No. 10 2005 048 184.1 filed Oct. 7, 2005, the disclosures of each of which are hereby incorporated by reference.

BACKGROUND OF THE INVENTION

1. Field of the Invention

The invention relates to a method for a rapid test of the quality of grains, crushed grains, and flours, by means of measuring the gluten aggregation.

2. Description of the Related Art

In their article "Qualitätsbeschreibung von Mehlen für nicht hefegelockerte feine Backwaren" ["Quality description of flours for fine baked goods not loosened with yeast"], in: *Getreide, Mehl und Brot* [Grain, Flour, and Bread] 52 (1998), 2, the authors Botterbrodt, Hanneforth, Lewandrowski, and Brümmer explain that in the description of flour quality, the questions as to what characteristic data characterize the quality, and what characteristic data possess informational value for the range of use stand in the foreground. The characteristic values of flour quality, e.g. the protein content, the wet gluten content, but also those obtained from baking experiments, such as the rapid mix test (RMT), are variables known for this purpose.

In the article, in connection with rapid testing of flours, the so-called knock-out test is mentioned, which was already described for the first time in 1997, in the journal "*Getreide, Mehl und Brot*," Issue 51, by the authors Hanneforth, Zwingelberg, and Gebhard. In this test, also known as the gluten aggregation test, the aggregation behavior of a flour/water suspension in a ratio of 1:1.2 to 1:1.5 is observed, using distilled water. The grain to be studied is brought to a certain temperature and weighed into the mixer top in a commercially available mixer (110 g, for example). The water is tempered to 23° C., for example, and also weighed into the mixer (132 g, for example).

The mixer is turned on and allowed to run at a medium level (at approximately 4500 rpm) for about 20 seconds. Then, the mixer top is scratched slightly, and subsequently the mixer is operated for another 20 seconds at the previous level. Then the mixer is stopped for a short time, and the actual measurement begins, whereby the mixer runs at a higher level (6250 rpm, for example). The measurement is recorded and the time period between start of measurement and end of measurement is determined. The end of the measurement is reached when the power consumption of 2 amperes is reached after the maximum. The goal and purpose of this test is to confirm wheat lots (e.g. of the E and A wheat groups) that have been delivered and marked accordingly, by means of a corresponding aggregation behavior.

For a determination of the time point of maximal gluten cross-linking, an ampere meter is connected with the mixer. As a result of the formation of the gluten lattice in the mass, the mixer experiences increasing resistance, which leads to increased power consumption and thus to an increase in the ampere number displayed.

However, a disadvantage in this method is the fact that identical electric motors can never be present in different devices, so that each device records different power consumption values, since different windings also bring different thermal general conditions with them.

Furthermore, the use of distilled water is not suitable for every sample, since it has been found that in the case of many samples, in the case of so-called weak flours, no aggregation takes place. A further disadvantage is the relatively large sample amount that is needed. Another decisive disadvantage, however, is the long testing time, whereby the preparatory method steps up to the start of the actual measurement are complicated and time-intensive.

SUMMARY OF THE INVENTION

The invention is therefore based on the task of conducting a rapid test of the type stated initially, in such a manner that more precise results are obtained independent of the device, with a minimized sample amount, even in the case of weak flours.

The invention accomplishes this task with the characteristics of the method according to the invention. Further advantageous embodiments of the invention are discussed below, whereby a particularly configured device is proposed for carrying out the method.

The decisive innovation as compared with the state of the art can be seen, in the method according to the invention, in that the force that occurs and is required for deformation is measured directly; this force increases slowly during aggregation, and then reaches a maximum. Thus, one is independent of thermal effects that could falsify the measurement. The torsion forces that the sample exerts, during the measurement, on the electric motor for the stirring paddle, for example, which motor is mounted so as to rotate, is transferred to the measurement devices, which works with expansion measurement strips, by way of a lever arm having a defined length. The software that accompanies the measurement process calculates the corresponding torque from the force and the known lever arm.

Alternatively, the force measurement can also take place directly, by way of the axle or the rotation of the beaker that is alternatively mounted to as to rotate.

BRIEF DESCRIPTION OF THE DRAWINGS

FIG. 6 shows the motor driving the measurement paddle and the measurement strips used in the method according to the invention.

DETAILED DESCRIPTION OF THE PREFERRED EMBODIMENTS

Figure 4:
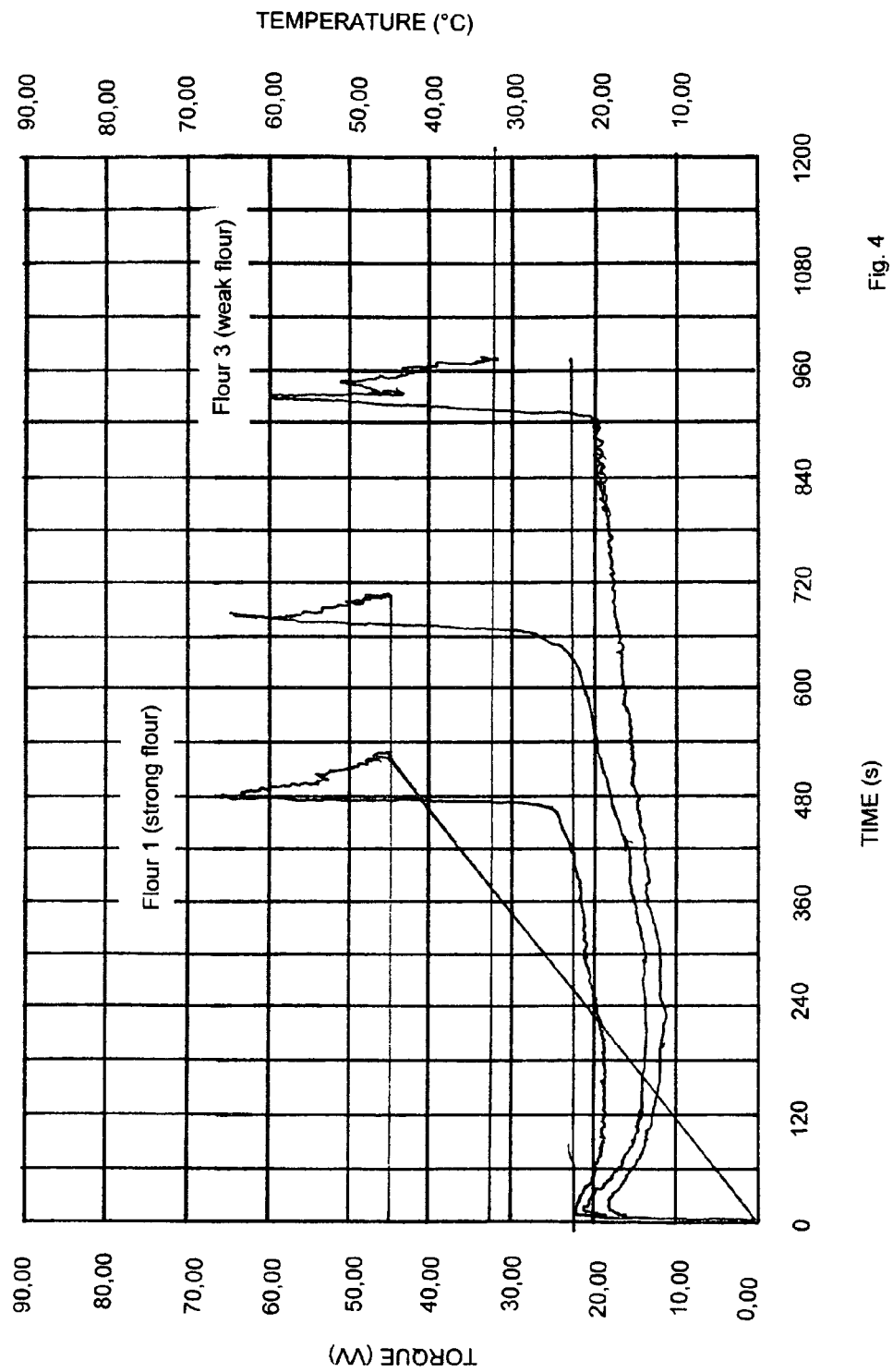
FIG. 4 is a diagram showing measurement procedures for three different types of flour.
Figure 4:
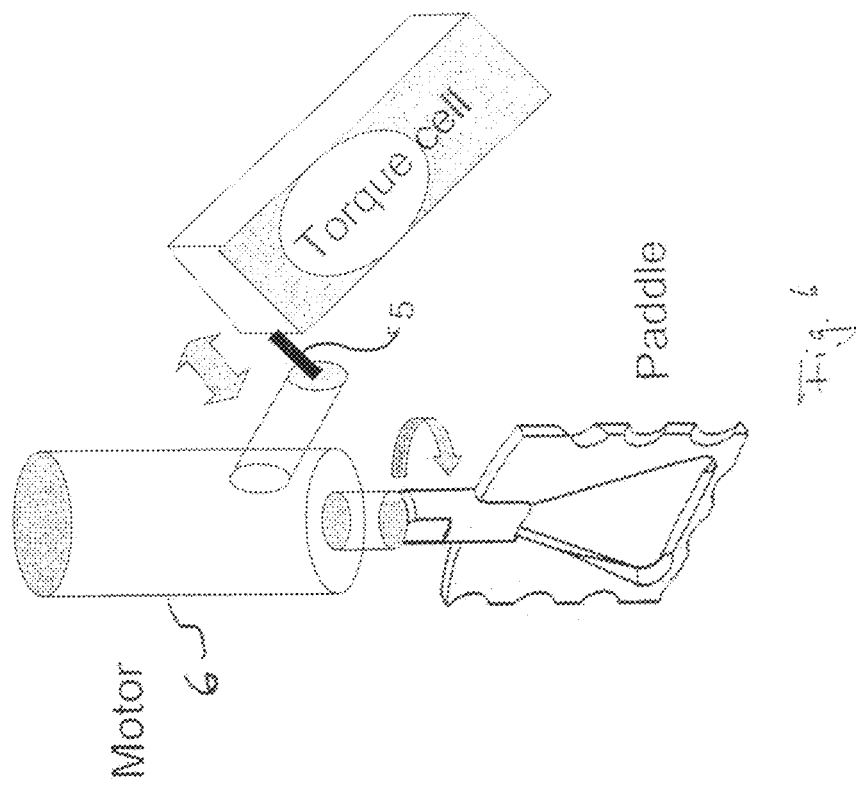

In FIG. 4, the measurement procedures for three different types of flour are shown, whereby a so-called strong flour, a so-called weak flour, and a flour that lies between the two were tested.

As is evident from this diagram, the strong flour already reaches the maximum after 480 seconds, while the weak flour has reached the aggregation maximum only after slightly more than 900 seconds.

Using the method according to the invention, it is therefore possible to differentiate different flours on the basis of their maxima.

Figure 3:
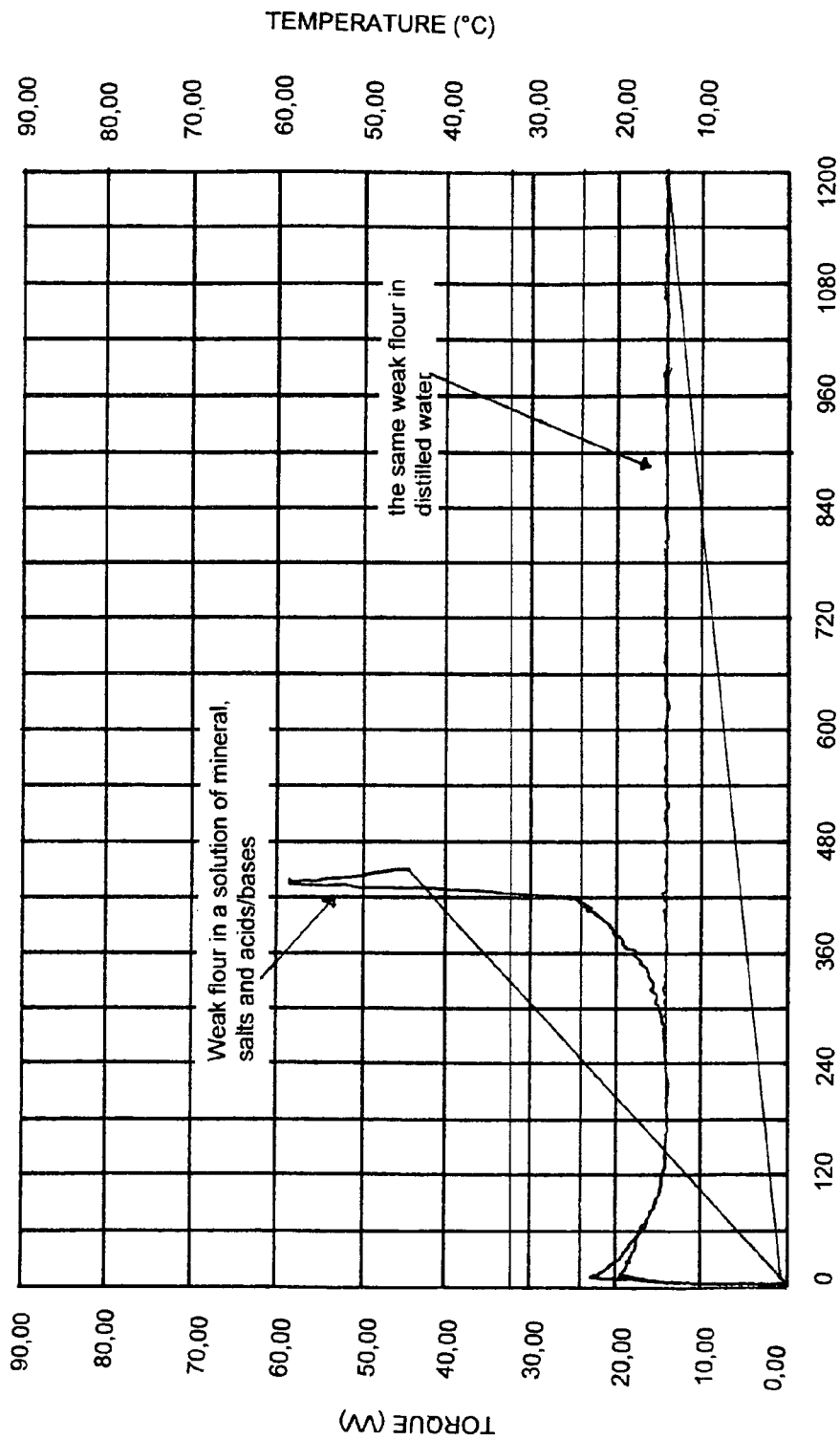
FIG. 3 is a diagram showing differentiation by means of a suspension medium.

In FIG. 3, it is shown that the aggregation behavior even of a weak flour can be verified using the method according to the invention, by means of the use of a solution of mineral salts and acids/bases, whereby here, the maximum is reached at an aggregation time of about 430 seconds. In contrast, the diagram for the same weak flour in distilled water (as in the state of the art) does not show any aggregation behavior.

In summary, it can be stated that using the method according to the invention, it is possible to reliably test the most varied flours, crushed grains, grains, and also baking mixtures with regard to their aggregation behavior.

For this purpose, in contrast to the state of the art, only a small test amount is needed. Experiments have shown that at a ratio of material to be tested and sample solution between 1:1.2 and 1:1.5, sample amounts of 10 to 20 g and solution amounts of approximately the same size are sufficient.

According to an embodiment, the suspension medium should have a conductivity of >5 µS and a pH<2 to 13.

According to an embodiment, it is provided that the speed of rotation of the measurement paddle is not supposed to exceed 6000 rpm. This is gentler for the sample, for one thing, and also gentler for the device, for another thing.

The speed of rotation, which can also be significantly lower than 6000 rpm (between 1000 and 6000 rpm), is predetermined by the software and automatically corrected by means of a constant comparison of the reference values and actual values.

In the evaluation, the temperature, which is continuously recorded, is also taken into consideration.

A preferred device for carrying out the method indicated above is discussed below. This is a device in which the drive and the measurement paddle are disposed above the sample beaker, so that the measurement paddle can be moved into the sample beaker from above. The electric motor that serves as the drive for the measurement paddle is mounted so as to rotate and connected with the force measurement device by means of a lever arm. The force measurement device works with expansion measurement strips. The torsion force exerted by the sample on the measurement paddle and from there on the electric motor is transferred to the expansion measurement strips by way of the lever arm. The corresponding torque is then calculated by the software, by forming the product of force and lever arm. The new geometry of the sample beaker and of the measurement paddle is particularly advantageous; this is because they are optimally coordinated with one another in terms of their shape. The measurement beaker has a smooth wall and is configured in cylinder shape. The outline of the measurement paddle is rectangular, and essentially agrees with the longitudinal cross-section of the smooth-walled stirring beaker. Recesses that are open to the outside are provided in the longitudinal side walls of the measurement paddle, allowing the stirred sample to pass through. Recesses are also provided in the inside surface of the measurement paddle.

The sample beaker, which has a simple structure in this manner, is preferably held on the device with a bayonet closure, and can consist of coated sheet steel or also of plastic.

The measurement paddle is also characterized by its simple, inexpensive structure.

A brushless motor, whose speed of rotation can be stabilized electronically, is proposed as a drive, whereas in the state of the art, alternating current motors with carbon brushes were used, in which the speed of rotation has to be manually adjusted by way of potentiometers, and thus no controlled regulation of the speed of rotation by means of an actual value/reference value comparison is possible during the measurement.

The measurement can begin immediately, without the preparatory actions described above, as soon as the measurement paddle has started to move.

Figure 1:
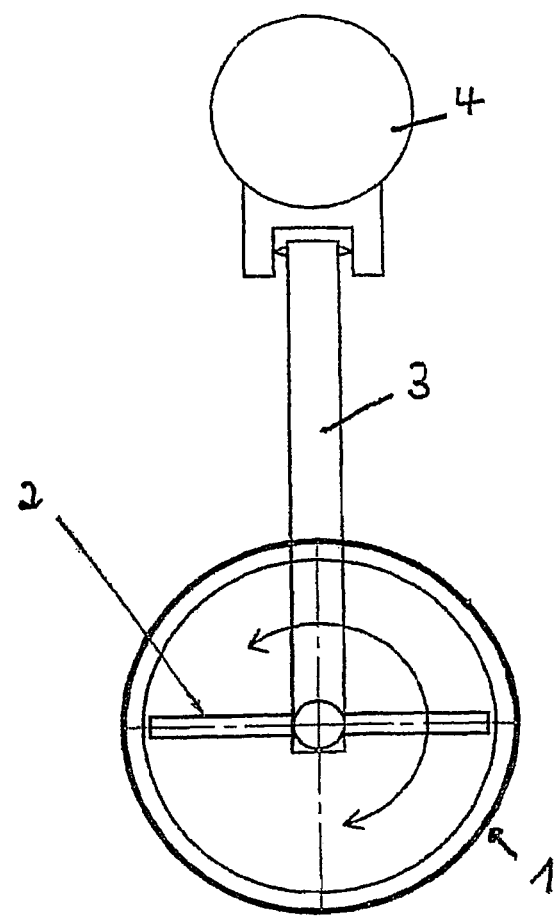
FIG. 1 shows a device for carrying out the method according to the invention.

FIG. 1 shows the schematic structure of the device for carrying out the method according to the invention.

Figure 5:
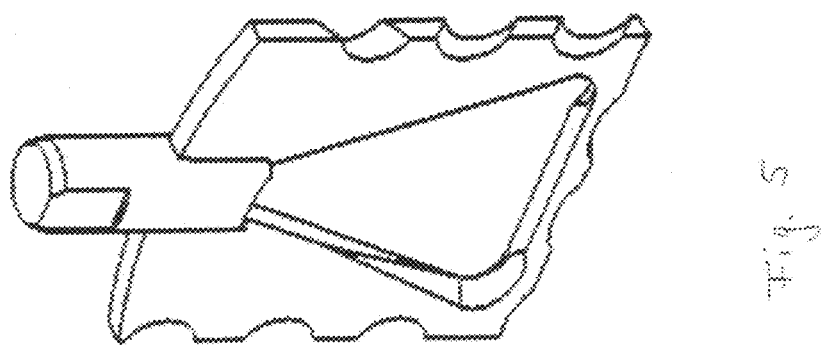
FIG. 5 shows a measurement paddle used in the method according to the invention.

The reference symbol 1 refers to the smooth-walled cylindrical sample beaker, in which a stirring measurement paddle 2 rotates. The measurement paddle 2 shown in FIG. 5 is driven by an electric motor 6, shown in FIG. 6, which is situated above the sample beaker 1. This electric motor 6 is mounted so as to rotate, and is connected with a measurement device 4 equipped with expansion measurement strips 5, by way of a lever arm 3. The force measured by the expansion measurement strips 5 is the torsion force that is produced by the resistance with which the sample counters the measurement paddle. The software calculates the corresponding torque from this force exerted on the measurement strips 5 and the defined length of the lever 3, and displays this in the diagram as a function of the running time.

Figure 2:
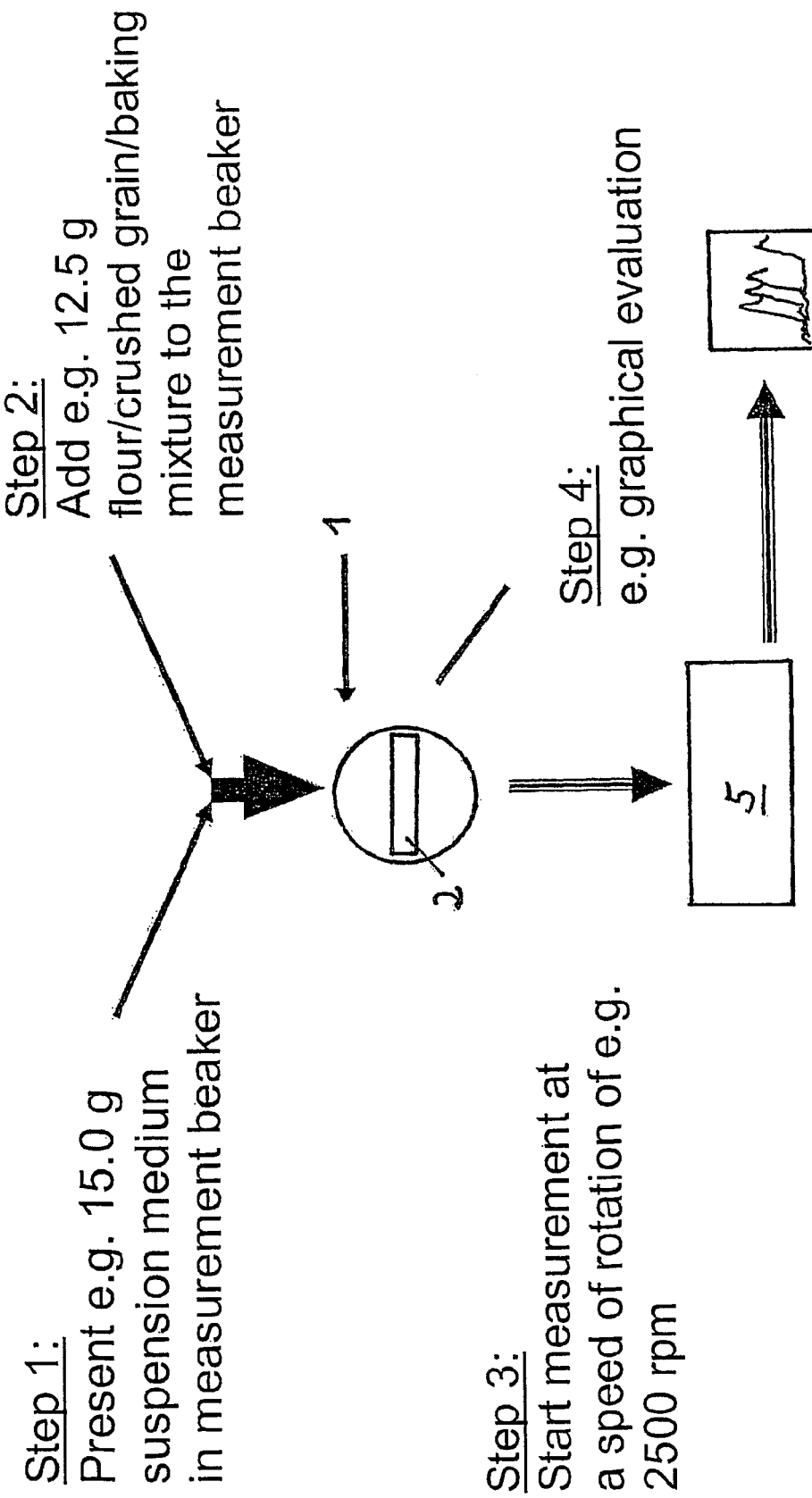
FIG. 2 is a flow schematic showing the method according to the invention.

FIG. 2 shows the flow schematic of the method according to the invention.

In the first step, the suspension medium (aqueous solution with salts, bases, acids) is introduced into the sample beaker 1. The amount is 15 g, for example. In the second step, the flour, crushed grain, baking mixture to be tested is introduced into the sample beaker 1. The amount is 12.5 g, for example. In the third step, the measurement begins with the start of the measurement paddle 2 at a speed of rotation of 2500 rpm, for example. The force is now measured, the corresponding torque is calculated from it, and in the fourth step, it is evaluated graphically. This is done by way of software that runs on the computers.

What is claimed is:

1. A device for measuring gluten aggregation, the device comprising:

an electric motor mounted to rotate at a speed of rotation between 1000 and 6000 rpm, the speed of rotation being able to be stabilized electronically;

a stirring paddle comprising a flat metal plate, the flat metal plate having an outline, longitudinal side edges, an inside surface, first recesses in the longitudinal side edges, and second recesses in the inside surface, the first recesses being exteriorly open, the second recesses being closed in themselves, and the stirring paddle being electrically driven by the electric motor;

a sample beaker, the sample beaker being smooth-walled, having a longitudinal cross-section, and being disposed below the electric motor in such a manner that the stirring paddle can be moved into the sample beaker from above, the longitudinal cross-section of the sample beaker essentially agreeing with the outline of the stirring paddle;

extensometric gauges able to measure torsion forces acting on the electric motor during rotation of the stirring paddle; and software able to monitor, control, and evaluate a measurement by the extensometric gauges of the torsion forces acting on the electric motor during rotation of the stirring paddle;

wherein via the electric motor, the stirring paddle, the sample beaker, the extensometric gauges, and the software, the device is configured to measure gluten aggregation of a sample of grains, crushed grains, or flours in an aqueous solution or suspension contained in the sample beaker, the aqueous solution or suspension including at least one of mineral salts, acids and bases.

2. The device according to claim 1, wherein the sample beaker further comprises a temperature-determining device for determining temperature.

3. The device according to claim 1, further comprising a lever arm having a lever length;
wherein force exerted by the stirring paddle onto the electric motor is transferred to the extensometric gauges by way of the lever arm to determine an amount of the force; and
wherein torque is calculated by the software from the lever length and the amount of the force.

* * * * *